United States Patent [19]

Case et al.

[11] 3,946,023

[45] Mar. 23, 1976

[54] MANUFACTURE OF 1,1′-DIALKYL-4,4′-BIPYRIDYLIUM SALTS

[75] Inventors: John Reginald Case; Geoffrey James Moore, both of Runcorn, England

[73] Assignee: Imperial Chemical Industries Limited, London, England

[22] Filed: Mar. 11, 1975

[21] Appl. No.: 557,258

Related U.S. Application Data

[63] Continuation of Ser. No. 357,655, May 7, 1973, abandoned.

[30] Foreign Application Priority Data

June 8, 1972 United Kingdom............... 26804/72

[52] U.S. Cl..................... 260/294.8 R; 260/296 D

[51] Int. Cl.$^2$........................................ C07D 213/74
[58] Field of Search.................. 260/296 D, 294.8 R

[56] References Cited
UNITED STATES PATENTS 3,326,926    6/1967    Homer........................... 260/296 D Primary Examiner—Alan L. Rotman
Attorney, Agent, or Firm—Cushman, Darby & Cushman

[57] ABSTRACT

A 1,1′-dialkyl-4,4′-bipyridylium salt is prepared by reacting the corresponding 4,4′-bipyridyl with a diloweralkylsulphate in the presence of a mineral acid.

5 Claims, No Drawings

MANUFACTURE OF 1,1'-DIALKYL-4,4'-BIPYRIDYLIUM SALTS

This is a continuation of application Ser. No. 357,655 filed May 7, 1973, now abandoned.

BACKGROUND OF THE INVENTION

This invention relates to the manufacture of 1,1'-dialkyl-4,4'-bipyridylium salts.

It is known that dialkylsulphates, for example dimethylsulphate, may be used as quaternising agents in the preparation of 4,4'-bipyridylium salts from 4,4'-bipyridyls. In the known reaction it is usual to employ at least the stoichiometric proportion of the dialkylsulphate for the formation of the alkylsulphate salt, for example in the formation of the dimethosulphate:

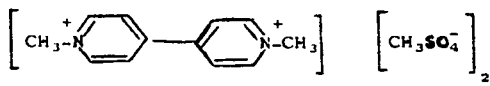

from 4,4'-bipyridyl itself, at least 2 moles of dimethylsulphate are used per mole of 4,4'-bipyridyl.

The aforesaid reaction has the disadvantage that only up to half of the alkyl groups in the dialkylsulphate are utilised in the production of the 1,1'-dialkyl-4,4'-bipyridylium cation.

SUMMARY OF THE INVENTION

It is an object of the invention to improve the efficiency of utilisation of the alkyl groups when a dialkyl sulphate is employed as quaternising agent. According to the present invention there is provided a method of preparing a 1,1'-dialkyl-4,4'-bipyridylium salt wherein a 4,4'-bipyridyl is treated with a dialkylsulphate in the presence of a mineral acid.

The use of a dialkylsulphate in the presence of a mineral acid leads to greater efficiency in the utilisation of the alkyl groups since a bipyridylium salt can be obtained without the wasteful incorporation of one alkyl group in the anion for each alkyl group introduced into the cation.

DETAILED DESCRIPTION OF THE INVENTION

It is preferred to use sulphuric acid as the mineral acid but other mineral acids, for example hydrochloric acid, may be used either alone or together with sulphuric acid.

While it is an advantage of the process described herein that the molar ratio of dialkylsulphate to bipyridyl may be reduced to below the ratio of 2/1 it will be understood that it is desirable to use at least 1 mole of dialkylsulphate per mole of bipyridyl (i.e. at least the stoichiometric proportion required for formation of the 1,1'-dialkyl-4,4'-bipyridylium ion). Similarly it is preferred that the total number of moles of dialkylsulphate and mineral acid is at least 2 moles per mole of bipyridyl.

If desired, the mineral acid may be introduced in the form of its salt with the bipyridyl.

The process is preferably carried out at a temperature of at least 90°C; it is especially preferred to use a temperature of at least 125°C, for example from 150°C to 250°C.

Depending upon such factors as the time and temperature of the reaction, at least part of the bipyridyl may be converted into a monoquaternary 1-methyl-4-(4-pyridyl)-pyridinium salt instead of the diquaternary 1,1'-dimethyl-4,4'-bipyridylium salt. The monoquaternary salt may be converted into a diquaternary salt by known methods or may be recycled to the quaternisation process described herein.

While the process is especially applicable to the quaternisation of 4,4'-bipyridyl itself, quaternary salts of substituted 4,4'-bipyridyls may also be prepared by the process described herein, including salts of 4,4'-bipyridyls substituted in one or both of the pyridine nuclei with one or more alkyl groups, especially one or more alkyl groups having 1 to 4 carbon atoms (for example 2,2'-dimethyl-4,4'-bipyridyl and 2,6'-dimethyl-4,4'-bipyridyl).

It is believed that at least some of the 1,1'-dialkyl-4,4'-bipyridylium cations in the product are associated with sulphate ions, but the nature of the anions may depend to some extent upon the conditions used in the quaternisation process, especially upon the acidity and/or the water content of the reaction medium.

If desired, the 1,1'-di-alkyl-4,4'-bipyridylium salt may be separated from the reaction products by known methods. In general, however, the bipyridylium salts are obtained in a form which requires little treatment before they are suitable for use as herbicides. Thus in many cases the product mixture may require no more than some dilution with water (and possibly adjustment of pH) before it is ready for application. Other ingredients, for example corrosion inhibitors and surface-active agents may also be incorporated in the solution if desired.

The invention is illustrated by the following Examples.

EXAMPLE 1

A mixture of 4,4'-bipyridyl, concentrated sulphuric acid and dimethylsulphate, containing 1.0 mole of sulphuric acid and 1.0 mole of dimethylsulphate per mole of bipyridyl, was heated in a sealed tube at 200°C for 4 hours. After cooling, the product was dissolved in water and analysed colorimetrically and polarographically.

The conversion of 4,4'-bipyridyl into 1,1'-dimethyl-4,4'-bipyridylium ion was 77% and the conversion into 1-methyl-4-(4-pyridyl)-pyridinium ion was 23%.

EXAMPLE 2

A mixture of 4,4'-bipyridyl (10.0g, 0.064 mole), dimethylsulphate (6.1 ml, 8.1g, 0.064 mole), and concentrated hydrochloric acid (5.6 ml, 6.6g, 0.064 mole) was heated under autogeneous pressure in a sealed tube at 200°C for 2 hours. At the end of the reaction the contents of the tube were washed out with a little water and analysed colorimetrically and polarographically.

The conversion of 4,4'-bipyridyl into 1,1'-dimethyl-4,4'-bipyridylium ion was 65% and the conversion into 1-methyl-4-(4-pyridyl)-pyridinium ion was 31%.

EXAMPLE 3

A mixture of 4,4'-bipyridyl (5.0g, 0.032 mole), diemthylsulphate (3.05 ml, 4.05g, 0.032 mole), concentrated hydrochloric acid (2.8 ml, 3.3g, 0.032 mole), and water (5.0 ml) was heated under autogeneous pressure in a sealed tube at 200°C for 2 hours. At the end of the reaction the contents of the tube were washed out with water and analysed colorimetrically.

The conversion of 4,4'-bipyridyl into 1,1'-dimethyl-4,4'-bipyridylium ion was 84%.

We claim:

1. A method for preparing a 1,1'-diloweralkyl-4,4'-bipyridylium salt by reacting the corresponding 4,4'-bipyridyl with a diloweralkylsulphate, the improvement which comprises carrying out the said reaction in the presence of a mineral acid.

2. A method according to claim 1 wherein the mineral acid is sulphuric acid.

3. A method according to claim 1 wherein the reaction is carried out at a temperature in the range 90°C to 250°C.

4. A method according to claim 1 wherein the 4,4'-bipyridyl is 4,4'-bipyridyl itself.

5. A method according to claim 1 wherein the total number of moles of diloweralkylsulphate and mineral acid is at least 2 moles per mole of the 4,4'-bipyridyl.

* * * * *